(12) United States Patent
Kumar

(10) Patent No.: US 6,966,916 B2
(45) Date of Patent: Nov. 22, 2005

(54) DEVICE AND METHOD FOR SURGICAL REPAIR OF ABDOMINAL WALL HERNIAS

(76) Inventor: Sarbjeet S. Kumar, 2923 Old South 431, Springfield, TN (US) 37172

( * ) Notice: Subject to any disclaimer, the term of this patent is extended or adjusted under 35 U.S.C. 154(b) by 329 days.

(21) Appl. No.: 10/256,352

(22) Filed: Sep. 26, 2002

(65) Prior Publication Data

US 2004/0092969 A1    May 13, 2004

(51) Int. Cl.$^7$ .............................................. A61B 17/04
(52) U.S. Cl. ...................... 606/144; 606/148
(58) Field of Search ................ 606/139, 144, 606/151, 148

(56) References Cited

U.S. PATENT DOCUMENTS

| | | |
|---|---|---|
| 4,347,847 A | 9/1982 | Usher |
| 4,705,040 A | 11/1987 | Mueller et al. |
| 4,741,330 A * | 5/1988 | Hayhurst .................. 606/144 |
| 5,053,046 A * | 10/1991 | Janese ...................... 606/215 |
| RE34,021 E | 8/1992 | Mueller et al. |
| 5,176,692 A | 1/1993 | Wilk et al. |
| 5,281,237 A | 1/1994 | Gimpelson |
| 5,290,217 A | 3/1994 | Campos |
| 5,307,924 A | 5/1994 | Manosalva et al. |
| 5,318,543 A | 6/1994 | Ross et al. |
| 5,336,239 A | 8/1994 | Gimpelson |
| 5,341,823 A | 8/1994 | Manosalva et al. |
| 5,391,182 A * | 2/1995 | Chin ........................ 606/213 |
| 5,474,573 A * | 12/1995 | Hatcher ..................... 606/232 |
| 5,507,755 A * | 4/1996 | Gresl et al. ................ 606/139 |
| 5,685,856 A | 11/1997 | Lehrer |
| 6,224,616 B1 | 5/2001 | Kugel |
| 6,398,796 B2 * | 6/2002 | Levinson .................... 606/144 |
| 6,626,919 B1 * | 9/2003 | Swanstrom .................. 606/153 |
| 6,669,707 B1 * | 12/2003 | Swanstrom et al. ......... 606/153 |

* cited by examiner

*Primary Examiner*—Gary Jackson
(74) *Attorney, Agent, or Firm*—Waddey & Patterson; Mark J. Patterson

(57) ABSTRACT

The present invention discloses a surgical opening repair device and methods of use thereof. The device comprises an anchor attached to a suture. The device has been specifically manufactured and designed in order to overcome the currently existing obstacles which result when a surgical repair device remains in the abdominal cavity subsequent to the completion of a surgical procedure. The invention additionally discloses a method of surgical hernia by using the device disclosed herein. The present invention additionally discloses a method of repairing a laparoscopic opening which commonly results from a primary surgery. The method of repairing the laparoscopic opening quickly and efficiently closes the opening such that repair is complete even though materials that are foreign to the body remain in the body subsequent to the procedure.

14 Claims, 6 Drawing Sheets

DEVICE AND METHOD FOR SURGICAL REPAIR OF ABDOMINAL WALL HERNIAS

FIELD OF THE INVENTION

The claimed invention relates to the repair of surgical openings. More specifically, the present invention relates generally to surgical methods of repairing hernias.

BACKGROUND OF THE INVENTION

Surgeons have used various methods for repairing hernias, or closing openings in order to prevent the onset of complications for their patients. A hernia is a hole or a defect in the fascia and muscular layers of the abdominal wall. An incisional hernia occurs at the site of a previous surgical incision. As a means of background, the following information is known to be used by surgeons to assist their patients. However, the currently known information does not solve the problems solved by the current invention.

In a current method of repair, the hernia sac is dissected and opened and any organs contained in the sac are freed and replaced back into the abdomen. The size of the defect is measured and a piece of mesh is prepared so that it is large enough to overlap the edges of the hernia defect by 3–5 cm on all sides. In the present art, fixation of the mesh is performed by placement of sutures using a "suture-passer" device. Grasping and feeding of the suture in to the grasping arm of the "suturepasser," within the abdomen, is technically difficult and cumbersome because the laparoscopic camera provides a mono-planar view rather than a three-dimensional (3D) view only. Fixation or suturing of the mesh to the abdominal wall is technically difficult, especially in laparoscopic surgery. Additionally, fixation of mesh to the abdominal wall is also time consuming.

With regard to repairing a laparoscopic opening, in the current art, it is necessary to insert a suture through the musculo-fascial layer on each side of the laparoscopic opening. The small skin incision restricts visibility for the surgeon so that it is usually not possible to place a safe and a secure suture. Consequently, the alternative techniques involve passage of a suture, using a hollow needle, into the abdominal cavity through one side of the musculo-fascial layer at the edge of the laparoscopic opening. The suture is released and the needle is reinserted into the abdominal cavity through the musculo-fascial layer on the other side of the laparoscopic opening. The suture is fed into the grasping arm of the needle which is then withdrawn to the outside. Two ends of the suture are then tied together so that the musculo-fascial opening is closed.

U.S. Pat. No. Re. 34,021, by Mueller et al., discloses percutaneous fixation of hollow organs. More specifically, the patent discloses a percutaneous fixation device and methods for the fixation of a hollow organ of a living body to a body wall. The method of the invention for the percutaneous fixation of organs is characterized by the steps of inserting a hollow needle carrying a retaining device attached to a filament through the skin into the organ, releasing the retaining device from the needle, and fixing the organ by adjusting the tension on the filament and clamping the filament by means bearing on the exterior of the body, as described in column 3, lines 10–17. The patent discloses the use of this method specifically for the anchoring of hollow organs without the need for a complex operation. Organs such as the stomach, kidney, gallbladder, large and small bowel, urinary bladder and duodenum are specifically mentioned in column 7, lines 31–34.

U.S. Pat. No. 4,347,847, by Usher, discloses a method of hernia repair. More specifically, the patent discloses a method which comprises repairing hernias by suturing surgical mesh to tissues in flattened form by suturing through the border edges of the mesh to adjacent tissue and bridging the hernial defect, the surgical mesh having sufficient openings even when doubled to permit rapid tissue growth through it, as described in column 2, lines 9–14. The patent acknowledges that in repair of hernias, such as incisional and inguinal hernias and defects in the abdominal and chest walls, it is important to promote growth of the tissue through the mesh to provide additional strength to the repaired area, as discussed in column 7, lines 30–34. Accordingly, the utility of using a mesh material for repairing an incisional hernia has been disclosed.

U.S. Pat. No. 5,176,692, by Wilk et al., discloses a method and surgical instrument for repairing hernia. More specifically, the method comprises inserting a balloon and inflating it such that the hernia is sealed. Subsequently, as described in the abstract, an inert polymeric material is provided for inducing human tissue growth. The device used for inducing human tissue growth may be a device such as a mesh web made of a biologically inert and flexible polymeric material, as described in column 2, lines 34–36. The method disclosed in this patent is directed toward repair of abdominal wall hernias.

U.S. Pat. No. 5,290,217, by Campos, discloses a method and apparatus for hernia repair. More specifically, the technique disclosed is used for hernias of tissue within the human body. The patent discloses various materials that have been used in experimental or clinical hernia repairs, including, for example, polypropylene mesh, Dacron fabric, tantalum gauze and the like, as described in column 2, lines 2–4. The patent additionally discloses the use of a patch having a series of punch holes, preferably all around the periphery at an approximate spacing from the edge equal to the span of the surgical staples, and of a diameter approximating the width of one limb of the clip or staple applicator as further described in column 2, lines 66–68 and column 3, lines 1–2. The patent additionally discloses that the patch is used in endo-clip or endo-staple application for manipulating and attaching the patch over a defect, as detailed in column 4, lines 10–12.

U.S. Pat. No. 5,391,182, by Chin, discloses an apparatus and method for closing puncture wounds. More specifically, the patent provides an apparatus and method for threading the ends of a suture into the body through the facial tissue surrounding a puncture opening or wound and for looping the ends out of the body through the wound so as to create a suture loop which, upon tightening, reapposes the fascial tissue as described in detail in column 2, lines 30–36.

What is needed, then, is a method for the repair of surgical hernias and surgical openings, wherein the method removes the disadvantages and the technical difficulties associated with the art described above. Additionally, the needed method would provide the resolution to the issue of the difficulty of the removal of the T-bars, also known as anchors, from the body.

SUMMARY OF THE INVENTION

The present invention discloses methods of repairing surgical hernias, methods of repairing laparoscopic openings, and a surgical opening repair device. The present invention provides the advantage of minimizing the manipulations of suture advancements, release, grasping, feeding into and retrieving from the instruments. Additionally, the present invention relieves the surgeon of the difficulties encountered due to the lack of three-dimensional visualization. More specifically, the method of repairing a surgical hernia comprises providing a first anchor having a suture attached, providing a second anchor having a suture attached, providing a mesh patch having a peripheral area, rolling the mesh patch, passing the mesh patch through the abdominal wall by using a surgical port, unrolling the mesh patch, inserting the first anchor through the abdominal wall into the abdominal cavity, passing the first anchor through the peripheral area of the mesh patch, inserting the second anchor through the same opening of the skin layer that the first anchor passed through and through a separate opening of the abdominal wall musculo-fascial layer and into the abdominal cavity, passing the second anchor through the peripheral area of the mesh patch, pulling on the sutures attached to the anchors so that the mesh patch adjoins the abdominal wall, and tying the sutures attached to the anchors over a musculo-fascial bridge so that the mesh patch remains adjoined to the abdominal wall.

The method of repairing an opening in the abdominal wall, such as an openings created for the passage of a laparoscope (laparoscopic opening) comprises providing a first anchor having a suture attached, providing a second anchor having a suture attached, inserting the first anchor through the abdominal wall and into the abdominal cavity, inserting the second anchor through the abdominal wall and into the abdominal cavity, and tying the sutures that are attached to the anchors such that the laparoscopic opening is closed.

The surgical opening repair device disclosed herein comprises an anchor having a middle section, and a suture attached to the middle section of the anchor. The anchor has a predetermined length and diameter. As further described herein, in certain embodiments, the device may be constructed of a bio-compatible and non-absorbable material, such as titanium, that is permanently retained in the body. In alternate embodiments, the device may be constructed of a bio-compatible and absorbable material, such as Polyglycolic Acid and related polyesters, that dissolve in the body over a period of 60 to 120 days.

Accordingly, one object of the present invention is to provide a method for efficiently repairing a surgical hernia.

Another object of the present invention is to provide a method of repairing a surgical hernia that is easy to accomplish, quick to accomplish, and a method that does not require use of hardware on the external surface of the body of the patient.

Still another object of the present invention is to provide a surgical opening repair device that may be left in the abdominal cavity of a patient subsequent to the complete repair of a surgical opening. Such device may be dissolvable or absorbable by the body or may be constructed of a material that does not produce harmful side effects when the material remains present in the body.

Another object of the present invention is to provide a method of repairing the laparoscopic opening wherein the method is completed quickly, makes use of the skills common to surgeons, and allows the opening to be closed in a non-complicated manner.

DESCRIPTION OF THE PREFERRED EMBODIMENTS

Figure 1:
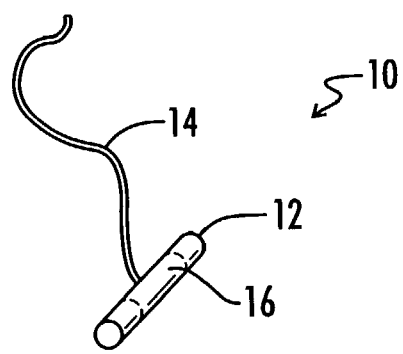
FIG. 1 is an isometric view of an anchor 12 having a suture 14 attached.

The present invention discloses devices and methods that may be used to repair surgical hernias or repair openings from laparoscopic ports or other surgical devices. The surgical opening repair device 10 comprises an anchor and a suture. The device is specifically designed and manufactured in order to overcome the problems associated with the previously available devices that were used to repair surgical openings.

The invention additionally discloses a novel method of repairing surgical hernias which provides surprising results. Briefly, the method comprises inserting a mesh patch into the abdominal cavity, inserting first and second anchors into the abdominal cavity and the mesh patch, pulling the sutures attached to the anchors so that the mesh patch that adjoins the abdominal wall, and tying the sutures together so that the mesh patch remains adjoined to the abdominal wall.

The present invention additionally discloses a method of repairing a laparoscopic opening. The method comprises inserting anchors through the abdominal wall at different locations and tying the sutures attached to those anchors together so that the laparoscopic opening is closed.

As used herein, a "surgical port" means any surgical device through which surgical devices may be transported. Accordingly, this definition includes, but is not limited to, laparoscopic ports, cannulae and needles.

As used herein, "nylon" means any of a family of high strength and resilient synthetic materials having a recurring amide group.

As used herein, a "non-absorbable material" means a material not being capable of absorption or break down by the human body. Non-absorbable materials include nylon.

As used herein, an "absorbable material" means material that is capable of being absorbed into or broken down by the body. An example of an absorbable material is polyglycolic acid.

As used herein, "bio-compatible" means a material that is compatible with the tissues, tissue lining, cellular lining, and other such components of the body. Such a bio-compatible material should not produce any negative effects to the body or the normal function thereof.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, the preferred methods and materials are described below. All publications, patent applications, patents, and other references mentioned herein are incorporated by reference in their entirety. Unless otherwise indicated, materials, methods, and examples described herein are illustrative only and not intended to be limiting.

As shown in FIGS. 1–3 and 5–12, the surgical opening repair device 10 comprises an anchor 12 and suture 14. The surgical opening repair device 10 may be used to repair laparoscopic openings, repair surgical hernias, repair abdominal wall hernias, as well as other surgical openings. More specifically, the anchor 12 has a middle section 16. The middle section 16 is defined as the middle one-third of the anchor 12. More specifically, the middle section 16 is the middle one-third of the length of the anchor 12, including the entire diameter of that section of the anchor 12. In certain embodiments, the anchor 12 has a length of about 1 centimeter and a diameter of about 0.2 centimeters. In other embodiments, the anchor 12 has a length of greater than 1 centimeter and a diameter of greater than about 0.2 centimeters. In certain embodiments, the anchor 12 is constructed of titanium. In still other embodiments, the anchor 12 is constructed of other non-absorbable material, such as surgical grade stainless steel. In other embodiments, the anchor 12 is constructed of an absorbable material such as polyglycolic acid or related polymers. Specific examples of related polymers include polydioxanone, polyglactin or poliglecaprone. The surgical opening repair device 10 is capable of repositioning specific items, such as a mesh patch 36 or a musculo-fascial layer 50, in order to repair an abdominal wall hernia or close a laparoscopic opening. As described in greater detail below, the anchor 12 is the rigid structure attached to the flexible suture 14. As the suture 14 is pulled to move the anchor 12, any item located between the anchor 12 and the source pulling the suture 14 is also moved in the same direction as the anchor 12.

As shown in FIG. 1, the suture 14 of the surgical opening repair device 10 is attached to the middle section 16 of the anchor 12. The type of attachment that is used is a permanent attachment such that the anchor 12 is not prematurely or unintentionally separated from the suture 14. In embodiments in which non-absorbable materials such as a nylon suture 14 and a titanium anchor 12 are used, the suture 14 is attached to the anchor 12 by infolding of the anchor metal upon the suture 14. Methods of attachment by infolding of the anchor metal are well known in the art. In other embodiments in which absorbable materials are used, the joint between the rigid anchor 12 and the flexible suture 14 is seamless since the underlying material is the same. For example, when an anchor 12 is constructed of polyglycolic acid and the suture 14 is constructed of polyglycolic acid, then the attachment is seamless. The manner of constructing both rigid and flexible polyglycolic acid materials is well known in the art. Also well known in the art is the manner of constructing rigid and flexible materials of the polymers related to polyglycolic acid, such as those described herein.

As described herein, the suture 14 is attached to the anchor 12 at a specific location. The suture 14 is attached within the middle section 16 of the anchor 12 because the additional length of the anchor 12 on each side of the middle section 16 is required in order to provide resistance when force is applied by pulling the suture 14. As attachment is defined within this invention, attachment of the suture 14 to the middle section 16 of the anchor 12 includes (1) attachment only within the middle section 16, (2) attachments having either multiple contact points being both inside and out of the middle section 16, and (3) a suture 14 attachment to an anchor 12 which is attached to the position other than the middle section 16, however, the type attachment allows the anchor 12 to maintain an orientation which is perpendicular to the suture 14 when the suture 14 is pulled.

Methods commonly known in the art should be used to provide attachment between the suture 14 and the anchor 12. In certain embodiments, the suture 14 and the anchor 12 will be constructed of identical material. In still other embodiments, the suture 14 and the anchor 12 will be constructed of non-identical materials. Methods are well known in the art for providing attachment between suture 14 and anchor 12 and the applicant is not providing any novelty with regard to manner of attachment of the suture 14 to the anchor 12.

The suture 14 may be constructed of an absorbable material. Construction of the suture 14 as an absorbable material allows the body to degrade the suture 14 such that surgical removal of the suture 14 is not required. A suture 14 constructed of an absorbable material will be absorbed, or degraded at a rate which is dependent upon the specific absorbable material used for construction. Polyglycolic acid is an absorbable material that may be used for the construction of suture 14.

Alternatively, the suture 14 may be constructed of a non-absorbable material. An example of non-absorbable material is nylon. Construction of the suture 14 by a material that is non-absorbable provides certain surgical benefits that are well known in the art. Many non-absorbable materials that are also bio-compatible, such as nylon, are well known in the art.

As mentioned above, the anchor 12 is constructed of a predetermined material. In certain embodiments, the anchor 12 is constructed of titanium. In other embodiments, the anchor 12 is constructed of polyglycolic acid. The advantage provided by constructing the anchor 12 of either titanium or polyglycolic acid is that either material may be left within the body. More specifically, titanium is a material that is not absorbed by the body. However, the material provides no long term threat if allowed to remain within an abdominal cavity subsequent to a surgical repair method. Accordingly, titanium is a bio-compatible material. Titanium additionally provides sufficient strength such that the anchor 12 is capable of performing the required tasks, which are further described below. In the embodiments in which the anchor 12 is constructed of polyglycolic acid, the material is readily absorbed by the body such that it no longer exists within the body after approximately ninety (90) days. Accordingly, specific surgical methods may require specific characteristics provided by a specific anchor 12 as well as a specific suture 14. Thus, in certain embodiments both the anchor 12 and the suture 14 may be constructed of polyglycolic acid. In other embodiments, the anchor may continue to be constructed of polyglycolic acid while the suture is constructed of an absorbable material, which is a material other than polyglycolic acid. Both absorbable and non-absorbable materials that may be used for the suture 14 are well known within the art. In still other embodiments it may be to the advantage in the specific surgical situation in order to use an anchor 12 that is constructed of titanium. A titanium anchor 12 may be attached to a suture 14 being constructed of any of the non-absorbable materials outlined above, such as nylon.

With regard to the dimensions of the suture 14, certain limitations to the specific dimensions must exist so that the surgical opening repair device 10, described herein, is capable of performing the described function. A suture 14 length that is sufficient for using the device and a repair method is a length that may be determined by the surgeon. In certain embodiments, the suture 14 will have a length of from about 10 centimeters to about 20 centimeters. The diameter of the suture 14 should be large enough to provide sufficient strength such that the suture is capable of maintaining the position of either the mesh patch or the tissue, as described below. However, a suture 14 having a diameter that is so large such that the suture 14 becomes cumbersome to handle is not desirable. Additionally, as described in detail below, the suture 14 will be tied to other sutures 14. Thus, a diameter that is prohibitive of the suture 14 being tied and holding a resistant force will not be desired.

Figure 2:
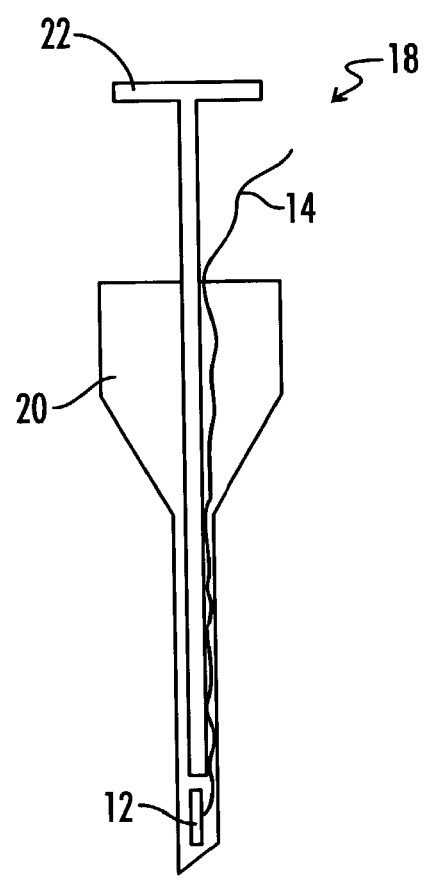
FIG. 2 is a planar view of the anchor 12 with suture 14 attached being loaded into a surgical probe 18. The anchor 12 can be discharged from the end of the surgical probe 18 by being forced out by the stylet 22.

As shown in FIGS. 2–8, the present invention discloses a method of repairing a surgical hernia. As mentioned above, in the present art, fixation of the mesh is performed by placement of sutures using a "suture-passer" device. Grasping and feeding of the suture in to the grasping arm of the "suture-passer," within the abdomen, is technically difficult and cumbersome because the laparoscopic camera provides a mono-planar view rather than a three-dimensional (3-D) view only. These problems are overcome and eliminated by this invention because it is not necessary to release and grasp the suture since the suture is permanently attached to the anchor. Tools commonly known in the art are used for inserting the anchors 12 through the skin layer 48, sub-cutaneous layer 52, musculo-fascial layer 50, peritoneum 54 and into the abdominal cavity 42, as well as for passing the anchors 12 through the peripheral area 38 of a mesh patch 36. As shown in FIGS. 3–7 and 9–12, the abdominal wall further comprises multiple layers. More specifically, the layers through which the anchors 12 pass include the skin layer 48, sub-cutaneous layer 52, musculo-fascial layer 50, and peritoneum 54. In certain embodiments of the present invention, the anchors 12 also pass through a mesh patch 36. Thus, as described herein, when an item, such as an anchor 12, is described as being in the abdominal cavity 42, it is located at a position that is interior to the skin layer 48, sub-cutaneous layer 52, musculo-fascial layer 50, and peritoneum 54. As shown in FIG. 2, a standard surgical probe 18 is used to accomplish such steps of insertion. More specifically, the surgical probe 18 provides a hollow tube section 20 into which the anchor 12 is inserted such that the suture 14 remains on the exterior side of the abdominal wall. The surgical probe 18 additionally includes a stylet 22 which is used to maneuver the anchor 12 through the hollow tube section 20 and through the opposite end of the surgical probe 18. Many types of surgical probes 18 are known in the art. Thus, surgical probes, insertion needles, etc. may be used to insert the anchors 12 as described herein.

Figure 3:
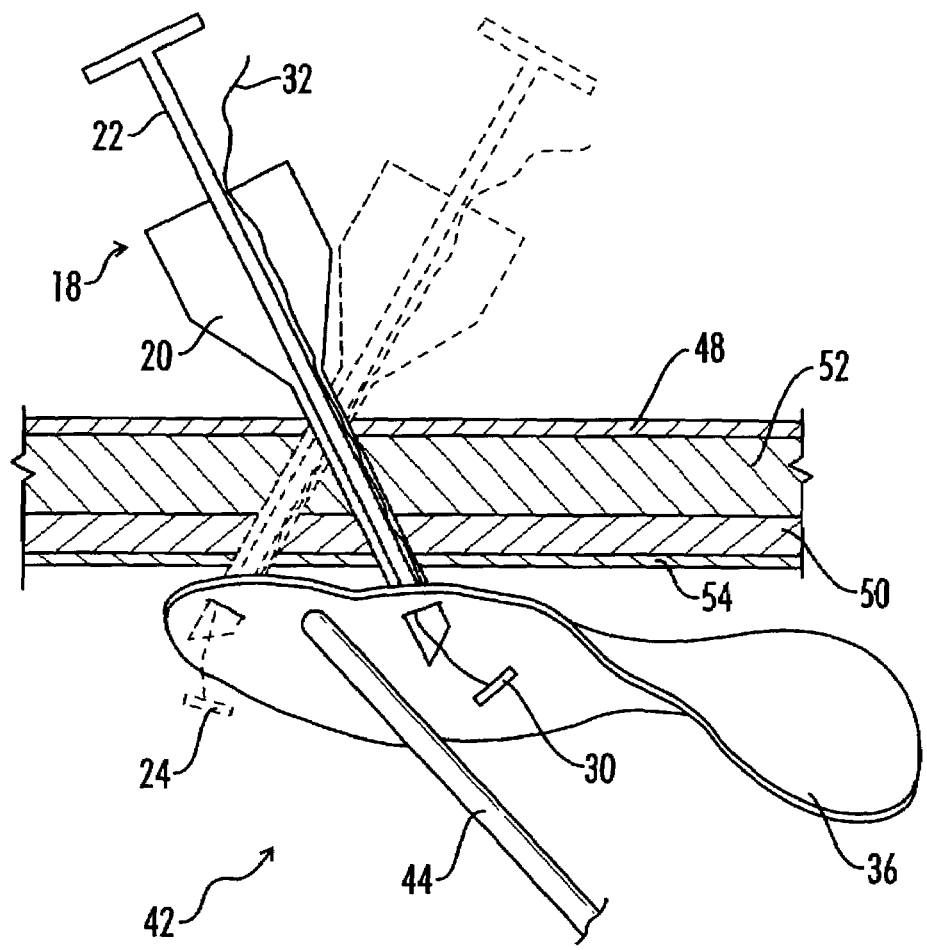
FIG. 3 illustrates the placement of an anchor through the abdominal wall and through the peripheral area of the mesh patch. The dashed surgical probe indicates the previous placement of the first anchor 24. The solid surgical probe indicates the current placement of the second anchor 30. Both probes enter and exit through the same opening in the skin layer. Each probe passes each anchor through separate and independent openings through the musculo-fascial layer 50 and the peritoneum 54.
Figure 5:
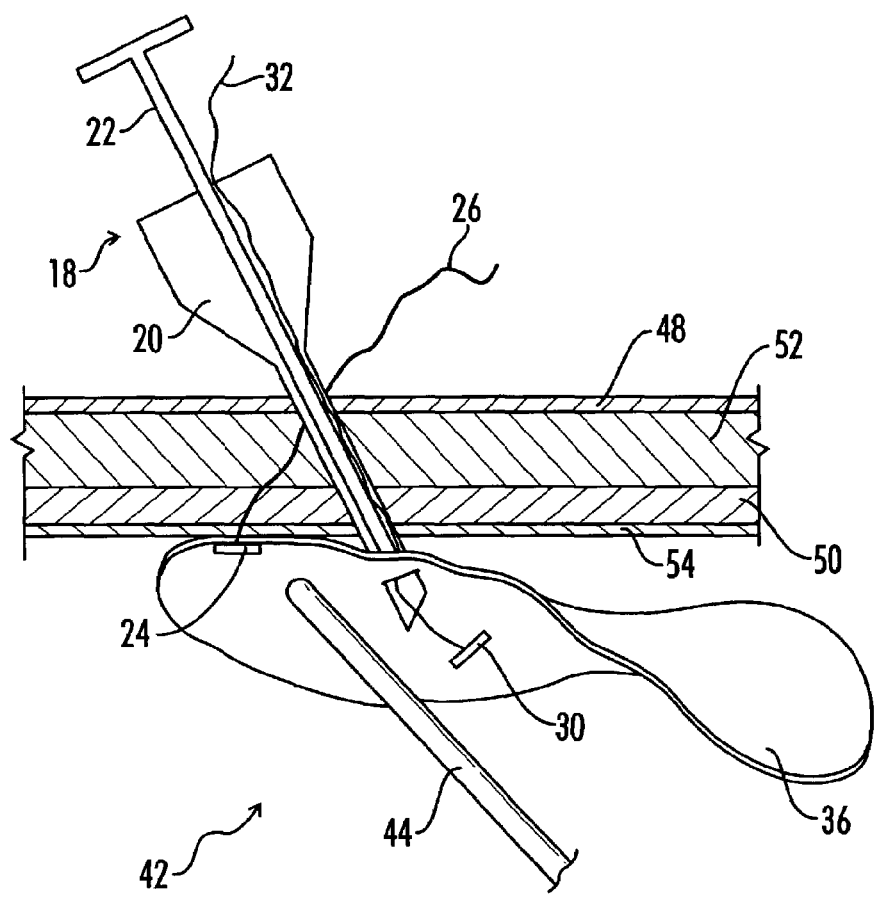
FIG. 5 is a cross sectional view of the continued placement and positioning of the first anchor 24 and the second anchor 30.
Figure 8:
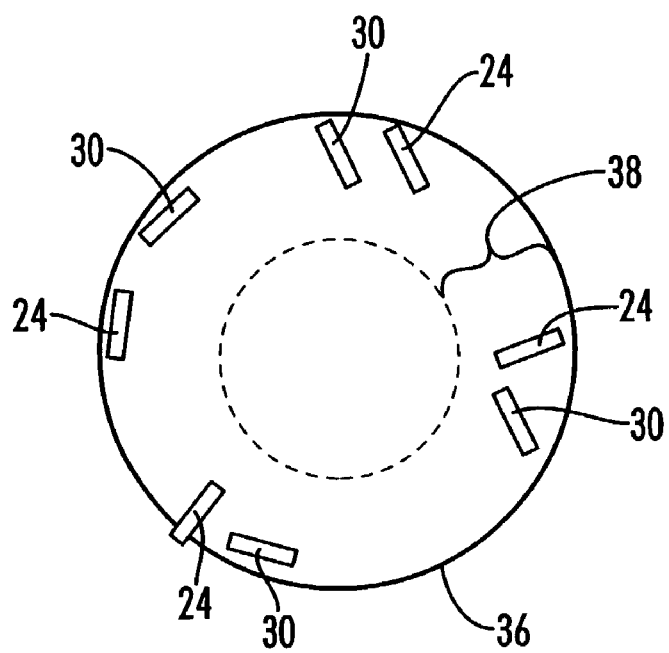
FIG. 8 is a planar view of the mesh patch demonstrating the various positions of the anchors which are holding the mesh patch against the abdominal wall by the force provided by tying the corresponding sutures together.

FIG. 3 outlines the first several steps of the method for repairing a surgical hernia. The hollow tube section 20 of the surgical probe 18 is used to position the anchor 12. More specifically, a surgical hernia is repaired by providing a first anchor 24. The first anchor 24 has a first suture 26 attached to it. The first suture 26 has a first distal portion 28 which may be used to grasp the first suture 26 in order to position the first anchor 24. As shown in FIG. 3, the hatched surgical probe 18 identifies the location of such probe when delivering the first anchor 24. The method additionally requires providing a second anchor 30 having a second suture 32 which has a second distal portion 34. The solid lined surgical probe 18 is the probe delivering the second anchor 30. As shown in FIG. 5, it is preferred to pull on the first distal portion 28 of the first suture 26 to position the first anchor 24 against the mesh patch 36 and the abdominal wall prior to inserting the second anchor 30. Additionally, it is necessary to provide a mesh patch 36 which has a peripheral area 38, as shown in FIG. 8. The mesh patch 36 is ultimately positioned adjacent to the abdominal wall such that the mesh patch 36 covers the surgical hernia in order to provide a repair of such hernia.

The mesh patch 36 is well known in the art. It is constructed of a mesh material which allows bodily tissue growth into the patch to further stabilize the position of the mesh patch at some point subsequent surgery. The mesh patch 36 is known to be constructed of many different materials, including but not limited to, Gortex, polytetrafluoroethylene or polypropylene. The present invention makes use of known mesh patches and the specific type of mesh patch to be used by a surgeon may be left to the personal preference of the surgeon.

It is common for the mesh patch 36 to have a peripheral area 38. The peripheral area 38 is the area within which an incision is made. More specifically, the peripheral area 38 is the area through which the anchors 12, also known as the first anchor 24 or the second anchor 30, are inserted such that the anchors 12 will provide a force upon the mesh patch 36 within the area of the peripheral area 38. It is also known, however, that the shape and the size of each mesh patch may differ based upon the specific surgical needs. Accordingly, the exact boundary of the peripheral area 38 is the border of about two (2) inches from the edge of a mesh patch 36 toward the center of the mesh patch 36. An example of the peripheral area 38 is shown in FIG. 8.

It is not shown, because it is very well known in the art, but, in order to insert the mesh patch 36 into the abdominal cavity 42, the mesh patch 36 is rolled in a manner similar to rolling cigarette paper, so that the mesh patch 36 is shaped to pass through a surgical port into the abdominal cavity 42. While within the abdominal cavity 42, the mesh patch 36 will naturally unroll so that the position of the mesh patch 36 can be manipulated. Additionally, unrolling may occur by repositioning of the mesh patch 36 with a guide 44, as further described below.

Figure 4:
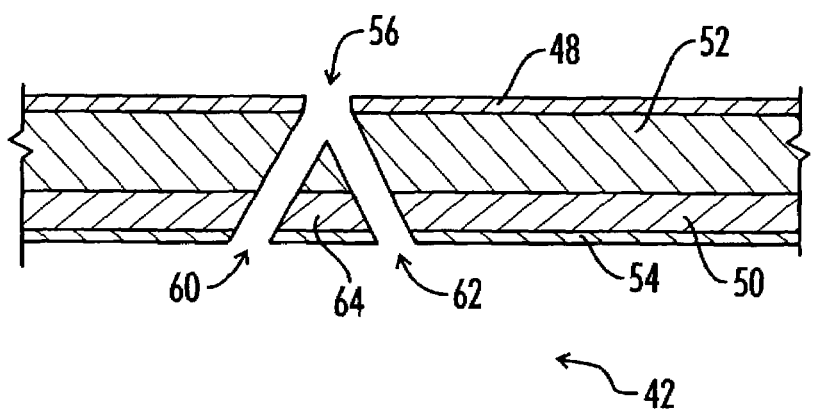
FIG. 4 is a cross sectional view of the openings created when the surgical probes place the anchors. Both surgical probes penetrate the skin layer 48 through the first opening of the skin layer 56. The surgical probe delivering the first anchor 24 creates the first opening of the abdominal wall 60 in order to pass the first anchor 24 through the musculo-fascial layer 50 and the peritoneum 54. The surgical probe delivering the second anchor 30 creates the second opening of the abdominal wall 62 in order to pass the second anchor 30 through the musculo-fascial layer 50 and the peritoneum 54. Also shown is the musculo-fascial bridge 64.

A beneficial aspect of the present method is the use of a single incision in the skin layer 48 for the delivery of each pair of anchors 12. As shown in FIG. 4, only a single opening of the skin layer 56 is needed. By modifying the angle of insertion of the instrument being used to insert the first anchor 24 and the second anchor 30, two independent and separate openings through the abdominal wall are created. By holding the surgical probe 18 at a first angle, upon insertion, a first opening 60 of the abdominal wall is created. When the surgical probe 18 is held at a second angle in order to deliver the second anchor 30, then a second opening 62 of the abdominal wall is created.

As shown in FIG. 5, in a preferred embodiment, after the first anchor 24 has been delivered by insertion through the first opening of the skin layer 56, through the first opening of the abdominal wall 60, and through the peripheral area 38 of the mesh patch 36, then the first distal portion 28 of the first suture 26 is pulled to position the first anchor 24 against the mesh patch 36. The mesh patch 36 is positioned against the peritoneum 54. FIG. 5 also shows the delivery of the second anchor 30 through the first opening of the skin layer 56, through the second opening of the abdominal wall 62, and through the peripheral area 38 of the mesh patch 36. Also shown is a guide 44 that is used to position the mesh patch 36 to be pierced by the surgical probe 18. The manner of puncturing, piercing, or inserting the surgical probe 18 into the mesh patch 36 is accomplished in an identical manner regardless of whether it is the first anchor 24 or any subsequent anchor being positioned.

As stated above, the method of repairing a surgical hernia comprises providing a first anchor 24 having a first suture 26 attached to it and the first suture 26 having a first distal portion 28. The next step requires providing a second anchor 30 having a second suture 32 connected to it with the second suture 32 having a second distal portion 34. The next step is providing a mesh patch 36 having a peripheral area 38. Next, the mesh patch 36 is rolled in order to allow compression for insertion into a surgical port. Once the mesh patch 36 is inserted into a surgical port, the mesh patch 36 is passed through the surgical port beyond the abdominal wall into the abdominal cavity 42. Once the mesh patch 36 is in the abdominal cavity 42 the mesh patch 36 is unrolled so that the peripheral area 38 of the mesh patch 36 is capable of being penetrated by the first anchor 24 and the second anchor 30 which are to be delivered by surgical probes 18. The next step is to insert the first anchor 24 through the abdominal wall into the abdominal cavity 42, wherein the first distal portion 28 of the first suture 26 which is attached to the first anchor 24 remains external to the abdominal wall. The next step consists of inserting the second anchor 30 through the abdominal wall into the abdominal cavity 42, wherein the second distal portion 34 of the second suture 32 which is attached to the second anchor 30 remains external to the abdominal wall. The relative rigidity of the abdominal wall allows for the surgical probe 18 to penetrate the abdominal wall by merely applying pressure. The sharp tip of the surgical probe 18 is capable of piercing through the content of the abdominal wall.

In continuing the method of repairing a surgical hernia, it is necessary to pass the first anchor 24 through the peripheral area 38 of the mesh patch 36. As best seen in FIG. 8, and as described previously, the peripheral area 38 of the mesh patch 36 is the external most boundary of the mesh patch 36. More specifically, the approximate two (2) inches that serve as the outermost boundary of the mesh patch 36 are to be considered the peripheral area 38. Since a mesh patch 36 is often times not rigid, it may be necessary to manipulate the position of the mesh patch 36 with a guide 44. Once the hole is pierced in the peripheral area 38 of the mesh patch 36, the stylet 22 is pushed to discharge either the first anchor 24 or the second anchor 30 from the hollow tube section 20 of the surgical probe 18. After doing so, as best seen in FIG. 5, the first distal portion 28 of the first suture 26 of the first anchor 24 is pulled in order to position the peripheral area 38 of the mesh patch 36 adjacent to the first anchor 24 and next to the abdominal wall. Likewise, after delivery of the second anchor 30, the second distal portion 34 of the second suture 32 of the second anchor 30 is pulled in order to position the mesh patch 36 adjacent to the abdominal wall.

Figure 6:
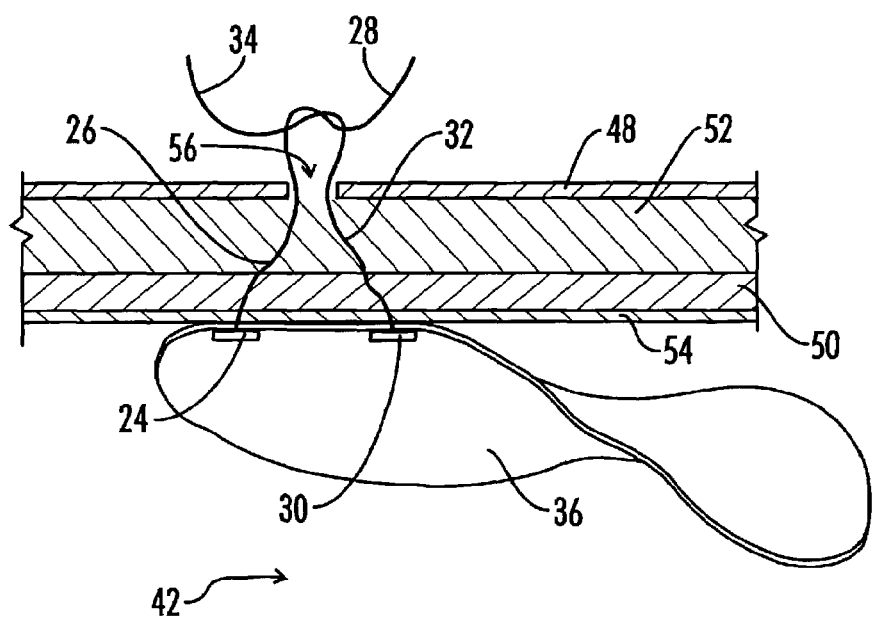
FIG. 6 is a view of the anchors being used to position and move the mesh patch into a proper location.
Figure 7:
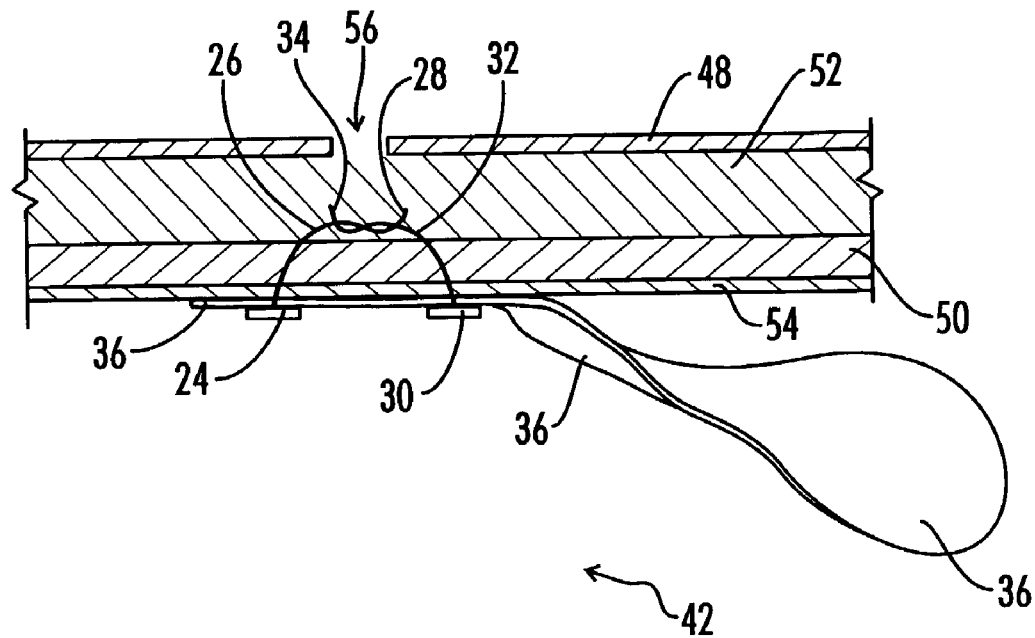
FIG. 7 is a planar view of the mesh patch being held in position against the abdominal wall by the anchors and sutures of the present invention.

As best seen in FIG. 6, after the first anchor 24 and the second anchor 30 have been positioned to place the mesh patch 36 against the peritoneum 54 of the abdominal wall, then the first distal portion 28 of the first suture 26 is tied to the second distal portion 34 of the second suture 32 so that the mesh patch 36 remains adjacent to, adjoined to, or connected to the abdominal wall. By pulling on the first distal portion 28 of the first suture 26 which is attached to the first anchor 24, the surgeon removes any slack that may have been present in the first suture 26. By pulling on the second distal portion 34 of the second suture 32 which is attached to the second anchor 30, any slack with any second suture 32 is removed such that the second anchor 30 positions the peripheral area 38 of the mesh patch 36 adjacent to the abdominal wall. By tying the first distal portion 28 to the second distal portion 34 such that no slack remains, as best seen in FIG. 7, the surgical hernia is repaired due to the positioning of the mesh patch 36 adjacent to the abdominal wall of the body.

The present method presents superior comfort to the patient. As described above, the sutures are tied together at a location that is beneath the skin layer 48. As shown in FIG. 7, the knot holding the first anchor 24 and the second anchor 30 in position is exterior to the musculo-fascial layer 50 and interior to the skin layer 48. The first opening of the skin layer 56 can be closed with either a bandage or one or two stitches. By tying together two sutures it is not necessary to use any additional materials or devices in order to crimp or position the tension on the suture. Reliance upon only the suture itself solves the problem of any failure or fault that might come from other devices, such as crimps, that may be used to hold the tension of a suture. Additionally, tying sutures allows a surgeon a quick way to secure the tension of the sutures. Finally, by tying the sutures, no material remains on the external surface of the patient. Other than a bandage or stitch, there is no material on the external surface of the patient and there is no opportunity for snagging, bumping, or irritating that which is not present. The lack of such bulky components on the exterior surface of the patient greatly enhances the comfort with which the patient proceeds during post operation recovery. Again, as best seen in FIG. 7, once the mesh patch 36 is tied adjacent to the abdominal wall, the method of repair is complete and the remaining steps of actual repair are handled inherently by the body.

As shown in FIG. 8, the function of the first anchors 24 and the second anchors 30 are to provide a non-flexible and resilient material which may be used to anchor and pull the mesh patch 36. Accordingly, the actual position of the first anchors 24 or the second anchors 30 is not relevant and is in fact due to the specific tension applied to the suture 14. Thus, some anchors may fortuitously line up in a parallel fashion while others may line up in a perpendicular manner. The final positioning is not relevant to the function of repairing surgical hernia.

In certain embodiments of the present invention, the first anchor 24 and the second anchor 30 have a length greater than about 0.9 centimeters and a diameter greater than about 0.2 centimeters. In certain embodiments, the anchor 12, also known as either a first anchor 24 or a second anchor 30, has a length of about 1.5 centimeters to 1 centimeter and a diameter of about 0.1 centimeter. In other embodiments, the anchor 12 has a length of about 1 centimeter to 0.5 centimeter and a diameter of about 0.1 centimeters. And yet in other embodiments, the anchor 12 has a length of from about 2 centimeters to about 1.5 centimeters and a diameter of about 0.1 centimeter.

In still other embodiments, the first anchor 24 and the second 30 are constructed of titanium. In still other embodiments, the first suture 26 attached to the first anchor 24 and the second suture 32 attached to the second anchor 30 are constructed of nylon. In still other embodiments, the first suture 26 attached to the first anchor 24 and the second suture 32 attached to the second anchor 30 are constructed of non-absorbable material.

The distance between the points of insertion through the abdominal wall, and corresponding point of insertion through the mesh patch 36, will generally be 1 centimeter. In certain embodiments, based upon the specific medical result desired or the preference of the surgeon involved, the distance between the points of the insertion into the abdominal wall may be less than 1 centimeter. In other embodiments, the distance between the points of insertion into the abdominal wall may be greater than 1 centimeter. In still other embodiments, the distance between the points of insertion through the abdominal wall may be about 2 centimeters. The specific distance between the points of insertion is variable to a certain degree and may be modified based upon the preference of the surgeon.

In certain embodiments, the first anchor 24 and the second anchor 30 are constructed of polyglycolic acid. In other embodiments of the present invention, when the first anchor 24 and the second anchor 30 are constructed of polyglycolic acid, the first suture 26 attached to the first anchor 24 and the second suture 32 attached to the second anchor 30 are constructed of polyglycolic acid. In still other embodiments, when the first anchor 24 and the second anchor 30 are constructed of polyglycolic acid, the first suture 26 attached to the first anchor 24 and the second suture 32 attached to the second anchor 30 are constructed of an absorbable material. In still another embodiment, the first anchor 24, the first suture 26, the second anchor 30, and the second suture 32 are constructed of a material that is readily absorbed by the body. Examples of absorbable material are disclosed herein.

In certain embodiments, the method of repairing a surgical hernia comprises providing a first anchor 24 having a length from about 2.5 centimeters to about 0.9 centimeters and a diameter from about 0.3 centimeters to about 0.09 centimeters. In certain embodiments the invention requires providing a second anchor 30 having a length from about 2.5 centimeters to about 0.9 centimeters and a diameter from about 0.3 centimeters to about 0.09 centimeters. In certain embodiments the invention requires providing a mesh patch 36 having a peripheral area 38, compressing the mesh patch, inserting the mesh patch through a port into the abdominal cavity 42, decompressing the mesh patch 36 so that the peripheral area 38 of the mesh patch 36 is capable of being penetrated by the first anchor 24 and the second anchor 30. As discussed previously, a guide 44 may be used to manipulate the mesh patch 36. In certain embodiments the method requires inserting the first anchor 24 through the abdominal wall into the abdominal cavity 42, wherein the first distal portion 28 of the first suture 26 which is attached to the first anchor 24 remains external to the abdominal wall, as best seen in FIG. 6. In still other embodiments, the present invention requires inserting the second anchor 30 through the abdominal wall into the abdominal cavity 42, wherein the second distal portion 34 of the second suture 32 which is attached to the second anchor 30 remains external to the abdominal wall. In certain embodiments, the present invention additionally requires piercing the peripheral area 38 of the mesh patch 36, wherein the opening of the peripheral area 38 of the mesh patch 36 is slightly larger than the diameter of either the first anchor 24 or the second anchor 30. Once the opening of the peripheral area 38 of the mesh patch 36 is provided, the first anchor 24 and/or the second anchor 30 are passed through the opening such that the either the first anchor 24 or the second anchor 30 engage the mesh patch 36 so that the mesh patch 36 may be positioned by pulling on either the first suture 26 or the second suture 32.

In certain embodiments of the present invention, the mesh patch 36 is pulled tightly against the abdominal wall. In other embodiments the mesh patch 36 is positioned in order merely contact the abdominal wall and the anchor 12 and suture 14 are used to retain the approximate positioning of the mesh patch 36. As shown in FIG. 8, the mesh patch 36 is ultimately attached to the abdominal wall by using multiple series of first anchors 24 and second anchors 30. As mentioned previously, the exact location of each anchor may be determined by each surgeon. The method of the present invention merely requires that the first suture 26 which is attached to the first anchor 24 be tied to the second suture 32 which is attached to the second anchor 30. By doing so, as shown in FIGS. 7 and 8, it is possible to place and attach a mesh patch 36 in order to repair a surgical hernia.

Tying the sutures can be accomplished by using any of the many knots that are well known in the surgical arts. Accordingly, in certain embodiments the first distal portion 28 that will be tied to the second distal portion 34 by using a square knot. In other embodiments, the first distal portion 28 will be tied to second distal portion 34 using multiple surgical knots. Use of standard surgical knots which are capable of providing sufficient resistance and a lack of slippage such that the initial anchor position is maintained, will be sufficient to tie the first distal portion 28 to the second distal portion 34. Examples of such surgical knots are well known in the art. Examples of surgical knots include, but are not limited to, square knots and surgeon's knots. In certain embodiments, the first anchor 24 and the second anchor 30 are transported through a hollow insertion needle in order to pass through the abdominal wall and into the abdominal cavity 42, and pierce the peripheral area 38 of the mesh patch 36.

Figure 9:
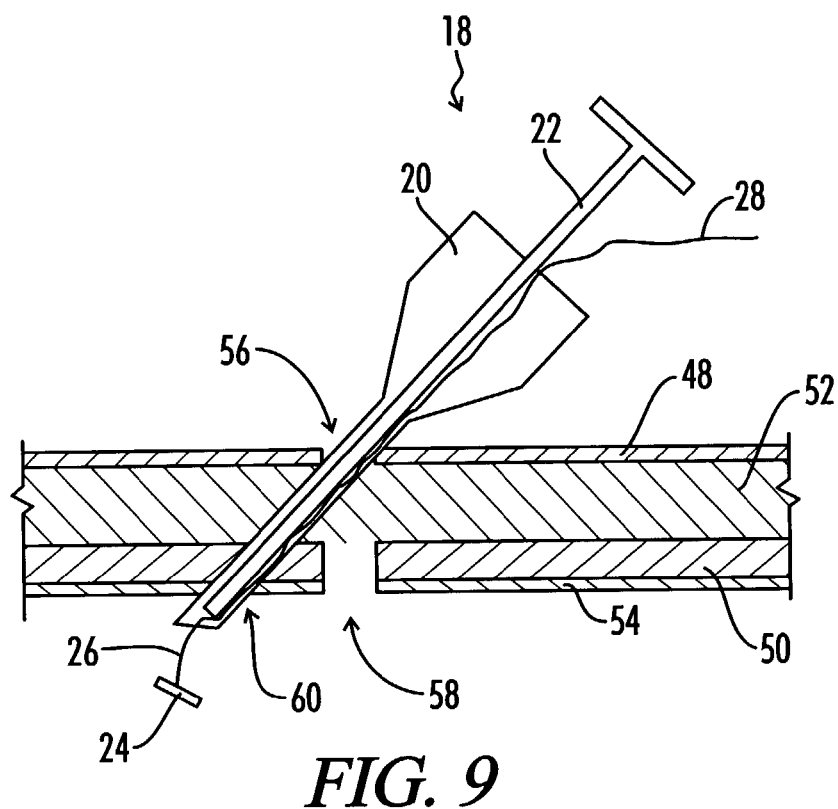
FIG. 9 is a planar view of the delivery of the first anchor 24 and first suture 26 through the abdominal wall so that they may be used to close a laparoscopic port opening.
Figure 10:
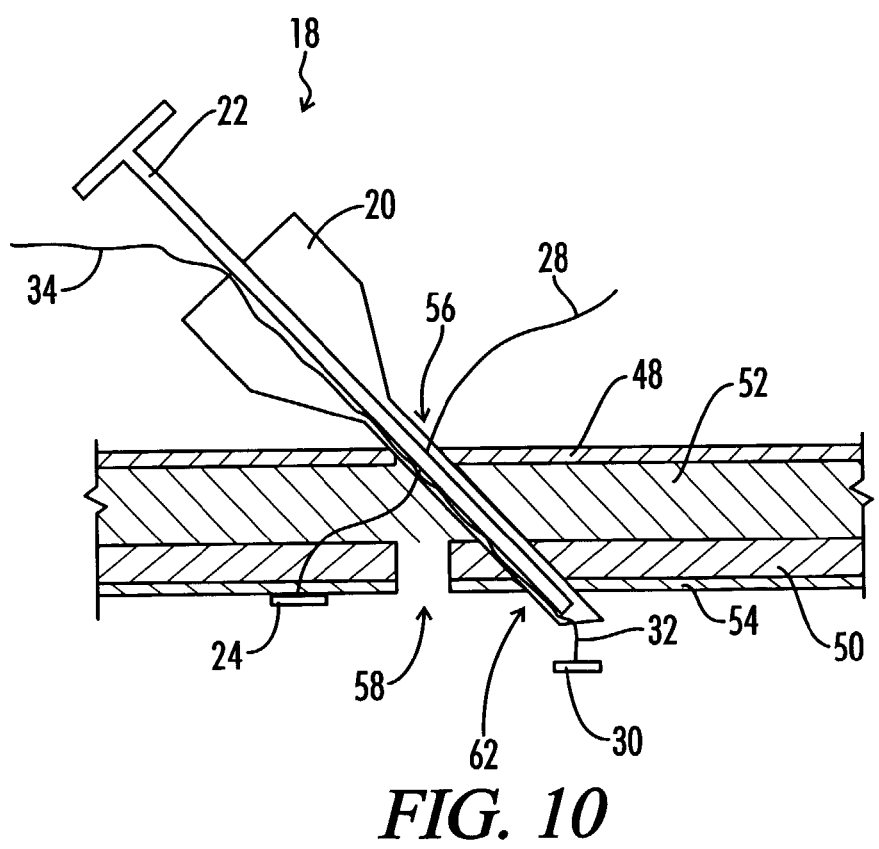
FIG. 10 is a planar view of the delivery of the second anchor 30 and second suture 32 through the abdominal wall so that they may be used to close a laparoscopic port opening.

Also disclosed herein is a method of repairing a laparoscopic opening. As previously described herein, in the current art, it is necessary to insert a suture through the musculo-fascial layer on each sidr of the laparoscopic opening. The small skin incision restricts visibility for the surgeon so that it is usually not possible to place a safe and a secure suture. Consequently, the alternative techniques involve passage of a suture, using a hollow needle, into the abdominal cavity through one side of the musculo-fascial layer at the edge of the laparoscopic opening. The suture is released and the needle is reinserted into the abdominal cavity through the musculo-fascial layer on the other side of the laparoscopic opening. The suture is fed into the a grasping arm of the needle which is then withdrawn to the outside. Two ends of the suture are then tied together so that the musculo-fascial opening is closed. The method disclosed herein generally differs from the method for repairing a surgical hernia in that the method for repairing a laparoscopic opening does not require the use of a mesh patch 36. As best shown in FIG. 9, the method for repairing a laparoscopic opening requires the use of certain devices described herein in order to close the opening. In a manner identical to the method of repairing a surgical hernia, the method of repairing a laparoscopic opening uses surgical probes 18, or equivalents thereof, to deliver the first anchor 24 and the second anchor 30. Furthermore, the first anchor 24 and the second anchor 30 are delivered through the first opening of the skin layer 56. As best shown in FIGS. 9 and 10, the first anchor 24 is delivered through the first opening of the abdominal wall 60 while the second anchor 30 is delivered through the second opening of the abdominal wall 62.

In certain embodiments, the method of repairing a laparoscopic opening comprises providing a first anchor 24 having a first suture 26 attached to it, providing a second anchor 30 having a second suture 32 attached to it, inserting the first anchor 24 through a first opening of the skin layer 56, through a first opening of the abdominal wall 60 and into the abdominal cavity 42, wherein the first distal portion 28 of the first suture 26 remains external to the abdominal wall, inserting the second anchor 30 through the first opening of the skin layer 56, through the second opening of the abdominal wall 62 and into the abdominal cavity 42, wherein a second distal portion 34 of the second suture 32 remain external to the abdominal wall, and tying the first distal portion 28 to the second distal portion 34 so that the laparoscopic opening is closed. As previously mentioned, tying includes making the use of knots that are well known in the art including, but not limited to, square knots and double knots.

Figure 11:
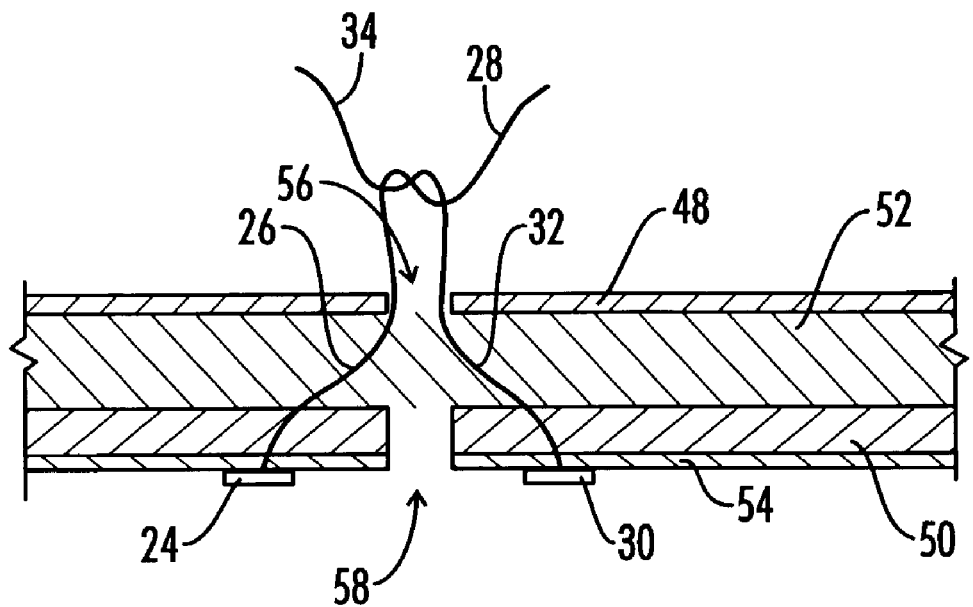
FIG. 11 is a planar view of the first suture 26 and the second suture 32 having been pulled in order to initially reposition the musculo-fascial layer 50 and the peritoneum 54 so that the musculo-fascial/peritoneum opening 58 starts to close.
Figure 12:
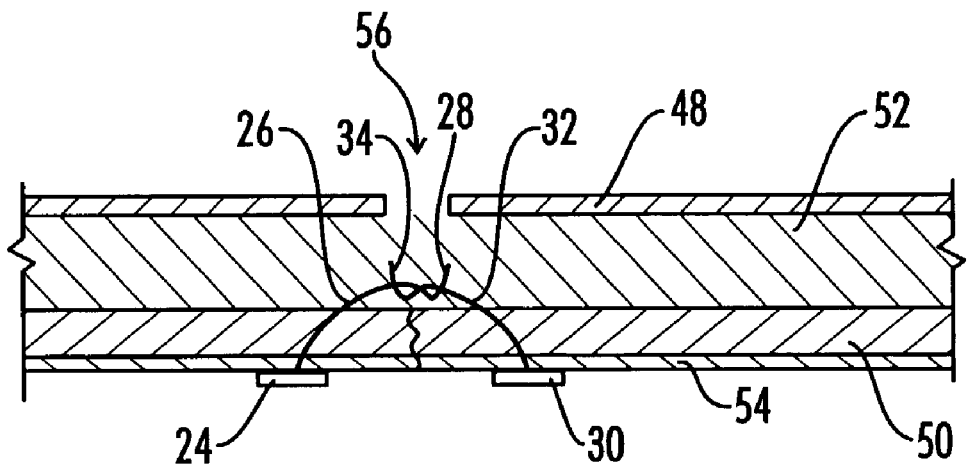
FIG. 12 is a planar view of the sutures being tied together in order to force closed the laparoscopic port opening, also known as the musculo-fascial/peritoneum opening 58.

As best seen in FIG. 9, in certain embodiments, surgical probes 18 are used to insert the first anchor 24 through the first opening of the skin layer 56, in this case the opening in the skin from the laparoscopic opening, through a first opening of the abdominal wall 60 and into the abdominal cavity 42. As previously stated, the abdominal wall is comprised of many layers. The layers through which the first anchor 24 and second anchor 30 are inserted include the sub-cutaneous layer 52, the musculo-fascial layer 50, and the peritoneum 54. The method of repairing a laparoscopic opening makes use of the identical devices that have been described herein. This method also makes use of the identical devices for placing the first anchor 24 and the second anchor 30. As shown in FIGS. 9–12, both the first anchor 24 and the second anchor 30 pass through the musculo-fascial layer 50 and peritoneum 54 of the abdominal wall at certain distances from the closest edge of the musculo-fascial/peritoneum opening 58. The musculo-fascial/peritoneum opening 58 is the laparoscopic opening. In certain embodiments, the surgical probe 18 is used to insert either the first anchor 24 or second anchor 30 at a distance of at least 0.5 centimeters and preferably up to 1.0 centimeter, from the closest edge of the laparoscopic opening, also known as the musculo-fascial/peritoneum opening 58. By positioning the anchors at such a distance from the laparoscopic opening, a sufficient amount of tissue of the abdominal wall is between either the first suture 26 or the second suture 32 and the laparoscopic opening such that the tissue of the abdominal wall may be manipulated or positioned by pulling on either the first suture 26 or the second suture 32, as shown in FIGS. 11 and 12. It is preferred to pull the first suture 26 tight in order to position the first anchor 24 against the peritoneum 54 prior to inserting the second anchor 30. In other embodiments, the surgical probe, or other hollow needle used for inserting the anchors, position either the first anchor 24 or the second anchor 30 at a distance of between 0.5 to 1.0 centimeters away from the closest edge of the laparoscopic opening. In still other embodiments, the specific positioning of the point of insertion for the first anchor 24 or the second anchor 30 is to be decided by the preference of the individual surgeon.

As best shown in FIG. 12, subsequent to the insertion and positioning of the first anchor 24 and the second anchor 30, the musculo-fascial/peritoneum opening 58, resulting from the previous insertion of a laparoscope, is closed. In certain embodiments, the musculo-fascial/peritoneum opening 58 is closed by grasping the first distal portion 28 of the first suture 26 and the second distal portion 34 of the second suture 32 and pulling so that the first anchor 24 is moved in a closer proximity to the second anchor 30 before the first distal portion 28 of the first suture 26 is tied to the second distal portion 34 of the second suture 32. Closing the musculo-fascial/peritoneum opening 58 allows the body to be in the best position to make a full recovery from the injury. As discussed when disclosing the method of repairing a surgical hernia, the sutures are tied together at a location that is external to the abdominal wall, including the musculo-fascial layer 50 and the peritoneum 54, and internal to the skin layer 48. The first opening of the skin layer 56 can be closed by any method known in the art. Preferably, the first opening of the skin layer 56 is closed by one or two stitches. Closing the first opening of the skin layer 56 encloses the knot which tied the sutures together, as seen in FIG. 12.

The anchors and sutures used in the method of repairing a laparoscopic opening may be of the wide variety of the types described herein. More specifically, in certain embodiments, the first anchor 24 and the second anchor 30 will have a length greater that about 0.9 centimeters and a diameter greater than 0.09 centimeters. In other embodiments, the first anchor 24 and the second anchor 30 will have a length of about 1 centimeter to about 1.5 centimeters and a diameter of about 0.1 centimeters. In certain embodiments, the first anchor 24 and the second anchor 30 may be constructed of titanium. And still other embodiments of the first anchor 24 and the second anchor 30 may be constructed of polyglycolic acid. In still other embodiments, the first suture 26 and the second suture 32 may be constructed of polyglycolic acid. In still other embodiments, the first suture 26 and the second suture 32 may be constructed of nylon. In still other embodiments, the first suture 26 and the second suture 32 may be constructed of other absorbable or non-absorbable materials.

This patent application incorporates by reference the entirety of all patents, references and publications disclosed herein.

Thus, although there have been described particular embodiments of the present invention of a new and useful Method for Surgical Repair of Abdominal Wall Hernias, it is not intended that such references be construed as limitations upon the scope of this invention except as set forth in the following claims.

What is claimed is:

1. A method of repairing a surgical hernia, comprising:
   providing a first anchor having a suture attached to the first anchor, the suture having a distal portion;
   providing a second anchor having a suture attached to the second anchor, the suture having a distal portion;

providing a mesh patch having a peripheral area;
rolling the mesh patch;
passing the mesh patch through a surgical port into an abdominal cavity;
unrolling the mesh patch so that the peripheral area of the mesh patch is capable of being penetrated by the first anchor and the second anchor;
inserting the first anchor through an abdominal wall into the abdominal cavity, wherein the distal portion of the suture attached to the first anchor remains external to the abdominal wall, wherein inserting the first anchor defines a first opening of a skin layer and a first opening of the abdominal wall;
passing the first anchor through the peripheral area of the mesh patch;
inserting the second anchor through the first opening of the skin layer and the abdominal wall into the abdominal cavity, wherein the distal portion of the suture attached to the second anchor remains external to the abdominal wall, wherein inserting the second anchor defines a second opening of the abdominal wall;
passing the second anchor through the peripheral area of the mesh patch;
pulling the distal portion of the suture attached to the first anchor and the distal portion of the suture attached to the second anchor so that the mesh patch adjoins the abdominal wall; and
tying the distal portion of the suture attached to the first anchor to the distal portion of the suture attached to the second anchor so that the mesh patch remains adjoined to the abdominal wall.

2. The method of claim 1, wherein the first anchor and the second anchor have a length greater than about 0.9 cm and a diameter greater than about 0.09 cm.

3. The method of claim 2, wherein the first anchor and the second anchor are constructed of titanium.

4. The method of claim 3, wherein the suture attached to the first anchor and the suture attached to the second anchor are constructed of nylon.

5. The method of claim 3, wherein the suture attached to the first anchor and the suture attached to the second anchor are constructed of a non-absorbable and bio-compatible material.

6. The method of claim 2, wherein the first anchor and second anchor are constructed of polyglycolic acid.

7. The method of claim 6, wherein the suture attached to the first anchor and the suture attached to the second anchor are constructed of polyglycolic acid.

8. The method of claim 6, wherein the suture attached to the first anchor and the suture attached to the second anchor are constructed of an absorbable material.

9. The method of claim 1, wherein the first anchor, the suture attached to the first anchor, the second anchor, and the suture attached to the second anchor are constructed of a material that is readily absorbed by a body.

10. A method of repairing a surgical hernia, comprising:
providing a first anchor having a suture attached to the first anchor, the suture having a distal portion, wherein the first anchor has a length from about 2.0 cm to about 0.9 cm and a diameter from about 0.3 cm to about 0.09 cm;
providing a second anchor having a suture attached to the second anchor, the suture having a distal portion, wherein the second anchor has a length from about 2.0 cm to about 0.9 cm and a diameter from about 0.3 cm to about 0.09 cm;
providing a mesh patch having a peripheral area;
compressing the mesh patch;
inserting the mesh patch through a port into an abdominal cavity;
decompressing the mesh patch so that the peripheral area of the mesh patch is capable of being penetrated by the first anchor and the second anchor;
inserting the first anchor through a first opening of a skin layer and a first opening of an abdominal wall into the abdominal cavity, wherein the distal portion of the suture attached to the first anchor remains external to the abdominal wall;
piercing the peripheral area of the mesh patch, wherein a first opening is created that is slightly larger than the diameter of the first anchor;
passing the first anchor through the first opening of the peripheral area of the mesh patch;
inserting the second anchor through the first opening of the skin layer and a second opening of the abdominal wall into the abdominal cavity, wherein the distal portion of the suture attached to the second anchor remains external to the abdominal wall;
piercing the peripheral area of the mesh patch, wherein a second opening is created that is slightly larger than the diameter of the second anchor;
passing the second anchor through the second opening of the peripheral area of the mesh patch;
pulling the distal portion of the suture attached to the first anchor and the distal portion of the suture attached to the second anchor so that the mesh patch adjoins the abdominal wall; and
tying the distal portion of the suture attached to the first anchor to the distal portion of the suture attached to the second anchor so that the mesh patch remains adjoined to the abdominal wall.

11. The method of claim 10, wherein the first anchor and the second anchor are constructed of titanium.

12. The method of claim 10, wherein the first anchor and the second anchor are constructed of polyglycolic acid.

13. The method of claim 12, wherein the suture attached to the first anchor and the suture attached to the second anchor are constructed of polyglycolic acid.

14. The method of claim 13, wherein inserting the first anchor and the second anchor through an abdominal wall into the abdominal cavity and piercing the peripheral area of the mesh patch further comprises transporting the first anchor and the second anchor through a hollow insertion needle.

* * * * *